United States Patent [19]

Wagner et al.

[11] Patent Number: 4,764,527
[45] Date of Patent: Aug. 16, 1988

[54] HYDROXYPYRAZOLE DERIVATIVES, COMPOSITION CONTAINING THEM AND THEIR USE AGAINST MICROORGANISMS

[75] Inventors: Klaus Wagner, Neustadt; Norbert Rieber, Mannheim; Ernst-Heinrich Pommer, Limburgerhof, all of Fed. Rep. of Germany

[73] Assignee: BASF Aktiengesellschaft, Rheinland-Pfalz, Fed. Rep. of Germany

[21] Appl. No.: 55,353

[22] Filed: May 29, 1987

[30] Foreign Application Priority Data

Jun. 19, 1986 [DE] Fed. Rep. of Germany ....... 3620579

[51] Int. Cl.$^4$ ................... A01N 43/56; C07D 231/16; C07D 231/12
[52] U.S. Cl. .................................... 514/407; 514/241; 514/242; 514/256; 514/358; 514/367; 514/369; 514/372; 514/373; 514/374; 514/378; 514/385; 514/389; 514/395; 514/399; 548/375; 548/376
[58] Field of Search ................ 548/375, 376; 514/407, 514/222, 241, 242, 256, 358, 367, 369, 372, 373, 374, 378, 385, 389, 395, 399

[56] References Cited

U.S. PATENT DOCUMENTS 4,673,429 6/1987 Rieber et al. ........................ 548/375

OTHER PUBLICATIONS

*Chemical Week*, (Jun. 21, 1972), p. 63, excerpt.
*Chemical Week*, (Jun. 26, 1972), p. 39, excerpt.
*Farm Chemicals Handbook*, 1976, p. D43.

Primary Examiner—Mary C. Lee
Assistant Examiner—Kurt G. Briscoe
Attorney, Agent, or Firm—Oblon, Fisher, Spivak, McClelland & Maier

[57] ABSTRACT

1-Hydroxypyrazoles of the formula

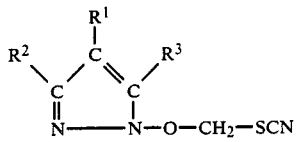

where $R^1$, $R^2$ and $R^3$ independently of one another are each hydrogen or halogen, and microbicides containing these compounds.

21 Claims, No Drawings

HYDROXYPYRAZOLE DERIVATIVES, COMPOSITION CONTAINING THEM AND THEIR USE AGAINST MICROORGANISMS

BACKGROUND OF THE INVENTION

1. Field of the Invention

The present invention relates to novel, useful hydroxypyrazole derivatives having fungicidal, bactericidal and algicidal activity, a process for their preparation, microbicides which contain these compounds as active ingredients and methods for controlling fungi, bacteria and algae (microorganisms).

2. Discussion of the Background

It is known that N-trichloromethylthio phthalimide (Chemical Week 1972, June 21st, page 63), tetramethylthiuram disulfide (Chemical Week 1972, July 26th, page 39) and 2-thiocyanomethylthiobenzothiazole (Farm Chemicals Handbook 1976, page D 43) can be used as fungicides or bactericides. However, their action is unsatisfactory. The alkyl-O-substituted and CN-alkyl-O-substituted derivatives of halogen-substituted 1-hydroxypyrazole have also been disclosed (No. DE-A-34 09 317), for example 4-chloro-1-methoxypyrazole and 4-chloro-1-cyanomethoxypyrazole.

SUMMARY OF THE INVENTION

We have found that 1-hydroxypyrazole derivatives of the formula I

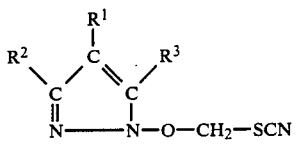

where $R^1$, $R^2$ and $R^3$ independently of one another are each hydrogen or halogen (chlorine, bromine or iodine), have excellent microbicidal activity and are more effective than the known active ingredients.

DETAILED DESCRIPTION OF THE PREFERRED EMBODIMENTS

Particularly preferred compounds are 4-halo-1-[(thiocyanato)-methoxy]-pyrazoles, in particular 4-chloro-1-[(thiocyanato)-methoxy]-pyrazole.

The compounds according to the invention are obtained by reacting a 1-hydroxypyrazole of the formula II

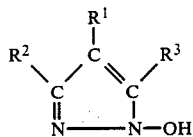

where $R^1$, $R^2$ and $R^3$ have the above meanings, with a thiocyanate of the formula III

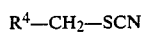

where $R^4$ is chlorine, bromine or iodine.

Compounds of the formula II are described in German Laid-Open Application DOS No. 3,205,456. Alkyl-O-substituted and CN-alkyl-O-substituted derivatives of 1-hydroxypyrazole having a nitrification-inhibiting action are described in German Laid-Open Application DOS No. 3,409,317. The compounds of the formula III are likewise known (German Laid-Open Application DOS No. 2,648,965 and European Pat. No. 65, 190).

To prepare the novel compounds, the reactants are allowed to react with one another, preferably in an inert solvent, such as an aliphatic or aromatic hydrocarbon or chlorohydrocarbon, eg. toluene or methylene chloride, an either, eg. diethyl ether or tetrahydrofuran, an alcohol, eg. tert.-butanol, a ketone, eg. acetone, a nitrile, eg. acetonitrile, or an amide, eg. N,N-dimethylformamide, in the presence of a base, for example a tertiary amine, pyridine, an alkali metal carbonate or an alkali metal alcoholate or hydride, at from −60° to 180° C., preferably from 20° to 80° C. The stated reaction may also be carried out in a two-phase system with phase-transfer catalysis. Chlorohydrocarbons, eg. methylene chloride, aqueous alkalis, eg. sodium hydroxide solution, and a phase-transfer catalyst, eg. tetra-n-butylammonium hydroxide, are preferably used for this purpose, at temperatures from 10° C. to the reflux temperature of the mixture of the reactants.

EXAMPLE 1

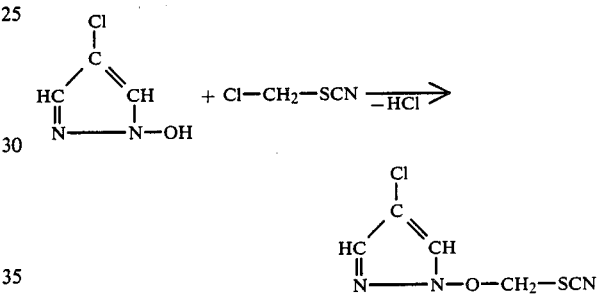

2.5 g (21 mMol) of 4-chloro-1-hydroxypyrazole in 50 ml of dry tetrahydrofuran were added dropwise to 1.4 g (35 mMol) of potassium hydride in 100 ml of dry tetrahydrofuran at from 10° to 15° C., and the mixture was then stirred for 30 minutes at room temperature. After the mixture had cooled to 15° C., 4.5 g (21 mMol) of chloromethylthiocyanate in 20 ml of dry tetrahydrofuran were slowly added dropwise, and stirring was continued for 5 days at room temperature. The reaction mixture was then partitioned between water and methylene chloride, and the organic phase was extracted with sodium carbonate solution, washed neutral and dried over magnesium sulfate. The solvent was stripped off in a rotary evaporator, after which the excess chloromethyl thiocyanate was distilled off from the residue (airbath at 90° C.) and 3.1 g (78% of theory) of 4-chloro-1-[(thiocyanato)-methoxy]-pyrazole (compound No. 1) were then distilled over (airbath at 160° C./2 mbar). After crystallization from ether/petroleum ether, the product had a melting point of 60° C.

EXAMPLE 2

50 ml of a 5% strength aqueous sodium hydroxide solution were added to 5 g (42 mMol) of 4-chloro-1-hydroxypyrazole, 13.5 g (126 mMol) of chloromethyl thiocyanate and 50 ml of methylene chloride. After the addition of 1 g (4 mMol) of tetra-n-butylammonium hydroxide, the mixture was stirred at room temperature for 24 hours. Thereafter, the organic phase was separated off, dried and evaporated down. Distillation of the residue under reduced pressure (airbath at 140° C./3 mbar) gave 5.7 g (71% of theory) of 4-chloro-1-[(thiocyanato)-methoxy]-pyrazole (compound No. 1), which was recrystallized from ether/petroleum ether (mp. 60° C.).

EXAMPLE 3

42 g (1.4 moles) of 80% strength by weight sodium hydride 1,000 ml of dry tetrahydrofuran were initially taken. 100 g (0.84 mole) of 4-chloro-1-hydroxypyrazole dissolved in 200 ml of dry tetrahydrofuran were added dropwise with gentle cooling. After stirring had been continued for 0.5 hour, 180.6 g (1.68 moles) of chloromethyl thiocyanate in 200 ml of dry tetrahydrofuran were added dropwise at 15° C. and stirring was continued at room temperature (20° C.) for 120 hours. Working up was then carried out similarly to Example 1. The crude product obtained after removal of the solvent was subjected to fractional distillation, 47.5 g of chloromethyl thiocyanate being recovered over a short distillation column (15 cm) at 90° C./36 mbar. Finally, 125.9 g (78% of theory) of compound 1 were distilled off at 90°–122° C./2 mbar.

EXAMPLE 4

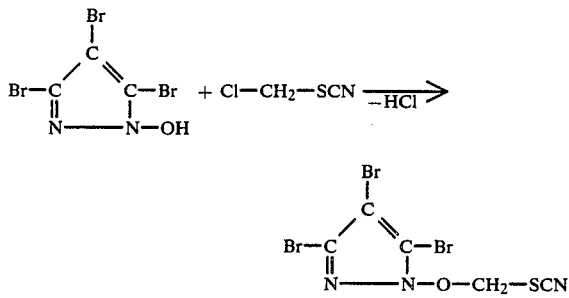

2.8 g of potassium hydride in 200 ml of dry tetrahydrofuran were initially taken, and 13.5 g (42 mMol) of 3,4,5-tribromo-1-hydroxypyrazole in 50 ml of dry tetrahydrofuran were added dropwise. The mixture was stirred for 0.5 hour, after which 9.0 g (84 mMol) of chloromethyl thiocyanate in 40 ml of dry tetrahydrofuran were added dropwise at 15° C. and stirring was continued for a further 120 hours. The mixture was then worked up as described in Example 1 to give 10.2 g (61% of theory) of compound 4, which was finally chromatographed over silica gel (1:1 ether/petroleum ether).

By appropriately modifying the preparation process, it is possible to obtain, for example, 3,4-dichloro-, 3,4,5-trichloro, 3-bromo-4-chloro-, 4-chloro-3-iodo-, 4-chloro-3,5-dibromo-, 4-chloro-3,5-diiodo, 4-bromo-3-chloro-, 4-bromo-3-iodo-, 4-bromo-3,5-dichloro-, 4-bromo-3,5diiodo-, 3,4-diiodo-, 3,4,5-triiodo-, 3-bromo-4-iodo-, 3-chloro-4-iodo-, 4-iodo-3,5-dibromo- and 4-iodo-3,5-dichloro-1-[thiocyanato-methoxy]pyrazole.

| Compound | $R^1$ | $R^2$ | $R^3$ | mp. [°C.] | $^1$H—NMR (CDCl$_3$) |
|---|---|---|---|---|---|
| 1 | Cl | H | H | 60 | 7.45 (s, 1H), 7.20 (s, 1H), 5.70 (s, 2H) |
| 2 | Br | H | H | 60 | 7.50 (s, 1H), 7.30 (s, 1H), 5.75 (s, 2H) |
| 3 | Br | Br | H | 81 | 7.50 (s, 1H), 5.75 (s, 2H) |
| 4 | Br | Br | Br | 103 | 5.80 (s) |
| 5 | I | H | H | 103 | 7.55 (s, 1H), 7.45 (s, 1H), 5.80 (s, 2H) |
| 6 | H | H | H | oil | 7.45 (m, 1H), 7.30 (m, 1H), 6.20 (t, 1H), 5.80 (s, 2H) |

The novel active ingredients are particularly useful for protecting various materials from degradation or destruction by bacteria or fungi or from attack and infestation by microorganisms. Materials in which the novel active ingredients can be incorporated as preservatives or microbicides are, for example, glues and adhesives, starch solutions, wax emulsions, clay emulsions, sizes, finishes, spinning baths, gelatin formulations, window putty, joint sealing materials, cooling lubricants, drilling oils, propellants, plastics dispersions, emulsion paints, textiles, leather, raw hides and cosmetics. The compounds are also useful as slime-controlling agents in the paper industry, in recooling units and in humidifying systems.

Examples of microorganisms which can be controlled with the novel compounds are the following: Staphylococcus aureus, Escherichia coli, Klebsiella pneumoniae, Citrobacter freundii, Proteus vulgaris, Pseudomonas aeruginosa, Desulfovibrio dusulfuricans, Streptoverticillium rubrireticuli, Aspergillus niger, Aspergillus versicolor, Penicillium funiculosum, Pencillium expansum, Penicillium glaucum, Peacilomyces varioti, Trichoderma viride, Chaetonium globosum, Aspergillus amstelodami, Phoma pigmentovora, Phoma violacea, Aureobasidium pullulans, Saccharomyces cerevisiae, Alternaria tenuis, Stemphylium macrosporoideum, Cladosporium herbarum, Cladosporium resinae, Candida albicans, Trichophyton mentagrophytes, Geotrichum candidans, Monilia sitophila, Scenedesmus quadricauda, Chlorella vulgaris, Nostoc muscorium, Oscillatoria limosa and Anabaena constricta.

The novel active ingredients are used in the form of formulations. The present invention accordingly also relates to agents or formulations which, in addition to conventional diluents and carriers, contain a compound of the formula I. The formulations, such as solutions, emulsions, suspensions, powders and pastes, are used in a conventional manner. The microbicides contain, for example, from 0.5 to 95% by weight of the active ingredient. The concentration usually chosen is from 0.001 to 5%, based on the weight of the material to be protected, of active ingredient; when used for water treatment, in oil production, in drilling and cutting oils, propellants, recooling units or humidifying systems or in the paper industry, amounts of from 5 to 500 ppm of active ingredient are sufficient. The active ingredients may also be mixed with other known microbicides. In many cases, this gives a synergistic effect. The list given below of bactericides and fungicides with which the novel compounds may be combined is intended to illustrate the possible combinations without imposing any restrictions. Combination with other active ingredients often increases the microbicidal action spectrum; a number of these microbicide mixtures also display synergistic effects, ie. the microbicidal activity of the combination product is greater than the sum of the activities of the individual components. These active ingredients can be mixed with the novel compounds in a weight ratio of from 1:1 to 100:1. Examples of active ingredients of this type are:

2-(thiocyanomethylthio)-benzothiazole

1-[2-(2,4-dichlorophenyl)-2-(2-propenyloxy)-ethyl]-1H-imidazole
2,4,5,6-tetrachloroisophthalodinitrile
methylene bisthiocyanate
tributyltin oxide, chloride, naphthenate, benzoate and salicylate
mercaptobenzothiazole
1,2-benzoisothiazolone and its alkali metal salts alkali metal compounds of N'-hydroxy-N-cyclohexylidazenium oxide
2-(methoxycarbonylamino)-benzimidazole
3-methyl-2-oxo-5-chlorothiazolin-4-one
trihydroxymethylnitromethane
glutardialdehyde
chloracetamide
polyhexamethylene bisguanide
5-chloro-2-methyl-4-isothiazolin-3-one and its magnesium salts
3,5-dimethyltetrahydro-1,3,5-2H-thiadiazine-2-thione
hexahydrotriazine
N-methylolchloroacetamide
2-n-octyl-4-isothiazolin-3-one
oxazolidines
bisoxazolidines
2,5-dihydro-2,5-dialkoxy-2,5-dialkylfurans
diethyldodecylbenzylammonium chloride
dimethyloctadecyldimethylbenzylammonium chloride
dimethyldidecylammonium chloride
dimethyldidodecylammonium chloride
trimethyltetradecylammonium chloride
benzyldimethyl-$C_{12}$-$C_{18}$-alkyl-ammonium chloride
dichlorobenzyldimethyldodecylammonium chloride
cetylpyridinium chloride
cetylpyridinium bromide
cetyltrimethylammonium chloride
laurylpyridinium chloride
laurylpyridinium bisulfate
benzyldodecyldi-($\beta$-hydroxyethyl)-ammonium chloride
dodecylbenzyldimethylammonium chloride
n-alkyldimethylbenzylammonium chloride (alkyl radicals: 40% $C_{12}$, 50% $C_{14}$, 10% $C_{16}$)
lauryldimethylethylammonium ethylsulfate
n-alkyldimethyl-(1-naphthylmethyl)-ammonium chloride (alkyl radicals: 98% $C_{12}$, 2% $C_{14}$)
cetyldimethylbenzylammonium chloride
lauryldimethylbenzylammonium chloride
Partner substances for the mixture
1,3-dimethylol-5,5-dimethylhydantoin
dimethylolurea
tetramethylolacetylenediurea
dimethylolglyoxalmonooureine
hexamethylenetetramine
glyoxal
glutardialdehyde
N-methylolchloroacetamide
1-(hydroxymethyl)-5,5-dimethylhydantoin
1,3-bis-(hydroxymethyl)-5,5-dimethylhydantoin
imidazolidinylurea
1-(3-chloroallyl)-3,5,7-triaza-1-azoniaadamantane chloride
1,3-bis-($\beta$-ethylhexyl)-5-methyl-5-aminohexahydropyrimidine
1,3,5-tris-(hydroxyethyl)-1,3,5-hexahydrotriazine
1,2-dibromo-2,4-dicyanobutane
5-bromo-5-nitro-1,3-dioxane
2-bromo-2-nitropropanediol
1,1'-hexamethylene-bis-[5-(4-chlorophenyl)-bisguanide]
4,4-diaminodiphenoxypropane
2-bromo-2-nitropropane-1,3-diol sorbic acid and its salts
p-hydroxybenzoic acid and its esters and salts
zinc 2-pyridinethiol-N-oxide
2-[(hydroxymethyl)-amino]-ethanol
dithio-2,2'-bis-(benzylamide)
5-chloro-2-(2,4-dichlorophenoxy)-phenol
thio-bis-(4-chlorophenol)
o-phenylphenol
chloromethyl diiodomethyl sulfone
p-chlorophenyl-3-iodopropargyl-formal.

In the use examples, the activities of novel compounds are described. The following known active ingredients were used for comparative purposes:

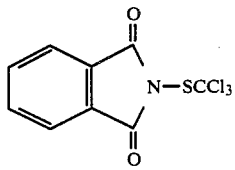
Active ingredient A

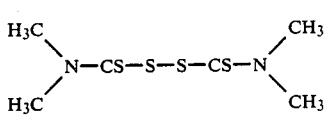
Active ingredient B

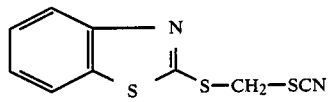
Active ingredient C

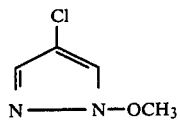
Active ingredient D

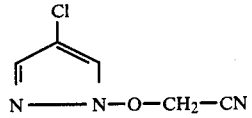
Active ingredient E

USE EXAMPLE 1

Fungicidal activity against *Aspergillus niger*

The active ingredients are added to a nutrient solution optimally suitable for growth of the fungus *Aspergillus niger*, in amounts of 100, 75, 50, 25, 10, 5 and 2.5 parts by weight per million parts of nutrient solution. 20 ml of each of the nutrient solutions treated in this manner are inoculated with 0.3 mg of Aspergillus spores in 100 ml glass flasks. The flasks are heated at 36° C. for 120 hours, after which the extent of fungal development, which preferentially takes place on the surface of the nutrient solution, is assessed.

The result of the experiment shows that, for example, compound 1 has a very good fungicidal action (100%) when used in the dilution 5 to 1 million parts by weight, whereas the known active ingredients A, B and C have no effect (0%) at this dilution.

USE EXAMPLE 2

Activity against the fungi *Paecilomyces varioti, Aureobasidium pullulans* and *Geotrichum candidans*.

To test the activity against fungi, the active ingredients are added to a nutrient solution optimally suitable for growth of the fungi *Paecilomyces varioti, Aureobasidium pullulans* and *Geotrichum candidans*, in amounts of 100, 50, 25, 12, 6, 3 and 1.5 parts by weight per million parts of nutrient solution. 10 ml of each of the mixtures of nutrient solution and active ingredient are introduced into sterile test tubes and inoculated with one drop of a spore suspension which contains $10^6$ conidia or cells. Incubation is carried out for 120 hours, after which samples are taken from those tubes which show no visible fungal growth and are transferred to nutrient media for fungi. The Table shows the dilution stage at which no growth of the fungi occurs after a sample has been transferred to the nutrient medium.

The result of the experiment shows that, for example, compounds 1, 2, 3, 4 and 6 have a good fungicidal action when used in a concentration of 6 ppm, whereas the same effect is obtained with the active ingredients A, B, C, D, and E only at 50 ppm.

USE EXAMPLE 3

Bactericidal activity against *Staphylococcus aureus, Escherichia coli, Proteus vulgaris* and *Pseudomonas aeruginosa*

The destruction values against bacteria are determined as follows: 5 ml of doubly concentrated nutrient broth are added to 5 ml of a dilution of the agent in water in sterile test tubes, and the components are mixed. The test batches contain 200, 100, 50, 25, 12, 6 and 3 parts by weight of active ingredient per million parts of nutrient broth. The tubes are then inoculated by adding one drop of 16 hour-old broth cultures of the bacteria strains *Staphylococcus aureus, Escherichia coli, Proteus vulgaris* and *Pseudomonas aeruginosa*, the cultures being diluted 1:10, and incubation is effected for 24 hours at 37° C. After this time, samples are transferred from the tubes to nutrient media for bacteria and likewise incubated for 24 hours at 37° C. The dilution stage at which no development of bacteria occurs after the sample has been transferred to the nutrient medium is stated as the destruction value.

The result of the experiment shows that, for example, compounds 1, 2, 3, 4 and 6 have a good bactericidal action when used in a concentration of 25 ppm, whereas the active ingredients C, D and E have this action only at 100 ppm.

USE EXAMPLE 4

Algicidal activity against green algae

To test the activity against green algae, the active ingredients are added, in amounts of 10, 7.5, 5, 2.5 and 1 parts by weight per million parts of nutrient solution, to a phosphate-rich nutrient solution which promotes multiplication of the monocellular green alga *Chlorella vulgaris*. 100 ml of each mixture of nutrient solution and active ingredient and of nutrient solution alone (control) are introduced into 300 ml conical flasks. The nutrient solution is inoculated with a suspension of the alga *Chlorella vulgaris* before the active ingredient is added; the cell density is brought to $10^6$ cells/ml of nutrient solution. The test batches are stored at room temperature and in the presence of light for 14 days, after which the activity is assessed.

The result of the experiment shows that, for example, compound 1 has a good action against algae when used in a concentration of 2.5 ppm.

USE EXAMPLE 5

The active ingredient 1, dissolved in propylene glycol, is added in amounts of 0.1, 0.05, 0.025, 0.01, 0.005, 0.0025 and 0.001%, based on the weight of the dispersion, to an aqueous dispersion which is based on a polyacrylate and is very susceptible to microorganisms. 100 ml of each test batch are then inoculated with a suspension of microorganisms which contains, as the microorganisms, *Staphylococcus aureus, Escherichia coli, Pseudomonas aeruginosa, Proteus vulgaris, Aspergillus niger, Penicillium funiculosum, Geotrichum candidans* and *Rhodotorula rubra*. The microorganism count in the inoculated dispersion is from $10^6$ to $10^7$ microorganisms/ml. Incubation is effected for 21 days at 25° C., after which the samples are transferred from the test batches to agar nutrient media suitable for the growth of bacteria, molds and yeasts, and these media are then incubated for 3 or 7 days in order to determine microorganisms which are still viable.

This experiment shows that as little as 0.005% of active ingredient 1 is sufficient to preserve an aqueous polyacrylate dispersion from attack by microorganisms.

We claim:

1. A 1-hydroxypyrazole derivative of the formula:

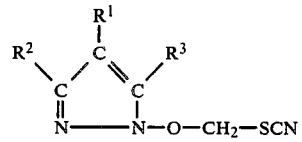

wherein $R^1$, $R^2$ and $R^3$ are each independently a hydrogen atom or a halogen atom.

2. The 1-hydroxypryazole derivative of claim 1, wherein said halogen is chlorine.

3. The 1-hydroxypryazole derivative of claim 1, wherein said halogen is bromine.

4. The 1-hydroxypyrazole derivative of claim 1, wherein said halogen is iodine.

5. The 1-hydroxypyrazole derivative of claim 1, wherein $R^1$ is a halogen atom.

6. The 1-hydroxypyrazole derivative of claim 1, wherein $R^2$ is a halogen atom.

7. The 1-hydroxypyrazole derivative of claim 1, wherein $R^3$ is a halogen atom.

8. 4-Halo-1[(thiocyanato)-methoxy]-pyrazole.

9. 4-Chloro-1-[(thiocyanato)-methoxy]-pyrazole.

10. The 1-hydroxypyrazole of claim 1, wherein $R^1$ is a bromine atom and $R^2$ and $R^3$ are both hydrogen atoms.

11. The 1-hydroxypyrazole derivative of claim 1, wherein $R^1$ and $R^2$ are both bromine and $R^3$ is a hydrogen atom.

12. The 1-hydroxypyrazole derivative of claim 1, wherein $R^1$, $R^2$ and $R^3$ are all bromine atoms.

13. The 1-hydroxypyrazole of claim 1, wherein $R^1$ is an iodine atom, and $R^2$ and $R^3$ are both hydrogen atoms.

14. The 1-hydroxypyrazole derivative of claim 1, wherein $R^1$, $R^2$ and $R^3$ are all hydrogen atoms.

15. A microbicidal composition comprising:

(1) a microbicidally effective amount of a 1-hydroxypyrazole derivative of the formula:

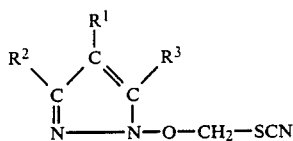

wherein $R^1$, $R^2$ and $R^3$ are each independently a hydrogen or a halogen atom; and (2) a solid or liquid carrier.

16. The microbicidal composition of claim 15, wherein said 1-hydroxypyrazole derivative is 4-halo-1-[(thiocyanato)-methoxy]-pyrazole.

17. The microbicidal composition of claim 15, wherein said 1-hydroxypyrazole derivative is 4-chloro-1-[(thiocyanato)-methoxy]-pyrazole.

18. The microbicidal composition of claim 15, comprising said 1-hydroxypyrazole derivative and at least one additional microbicide, said microbicide being present in an amount relative to said 1-hydroxypyrazole derivative to provide a weight ratio of microbicide to 1-hydroxypyrazole of from 1:1 to 100:1, wherein said mircrobicide is at least one member selected from the group consisting of 2-(thiocyanomethylthio)-benzothiazole; 1-[2-(2,4-dichlorophenyl)-2-(2-propenyloxy)-ethyl]-1H-imidazole; 2,4,5,6-tetrachloroisophthalodinitrile; methylene bisthiocyanate; tributyltin oxide, chloride, naphthenate, benzoate and salicylate; mercaptobenzothiazole; 1,2-benzoisothiazolone and its alkali metal salts, alkali metal compounds of N'-hydroxy-N-cyclohexylidazenium oxide; 2-(methoxycarbonylamino)-benzimidazole; 3-methyl-2-oxo-5-chloro-thiazolin-4-one; trihydroxymethylnitromethane; glutardialdehyde; chloracetamide; polyhexamethylene bisguanide; 5-chloro-2-methyl-4-isothiazolin-3-one and its magnesium salts; 3,5-dimethyltetrahydro-1,3,5,-2H-thiadiazinethione; hexahydrotriazine; N-methylolchloroacetamide; 2-n-octyl-4-isothiazolin-3-one; oxazolidines; bisoxazolidines; 2,5-dihydro-2,5-dialkoxy-2,5-dialkylfurans; diethyldodecylbenzylammonium chloride; dimethyloctadecyldimethylbenzylammonium chloride; dimethyldidecylammonium chloride; dimethyldidodecylammonium chloride; trimethyltetradecylammonium chloride; benzyldimethyl-$C_{12}$–$C_{18}$-alkyl-ammonium chloride; dichlorobenzyldimethyldodecylammonium chloride; cetylpyridinium chloride; cetylpyridinium bromide; cetyltrimethylammonium chloride; laurylpyridinium chloride; laurylpyridinium bisulfate; benzyldodecyldi-($\beta$-hydroxyethyl)-ammonium chloride; dodecylbenzyldimethylammonium chloride; n-alkyldimethylbenzylammonium chloride; lauryldimethylethylammonium ethylsulfate; n-alkyldimethyl-(1-naphthylmethyl)-ammonium chloride; cetyldimethylbenzylammonium chloride; lauryldimethylbenzylammonium chloride; 1,3-dimethylol-5,5-dimethylhydantoin; dimethylolurea; tetramethylolacetylenediurea; dimethylolglyoxalmonoureine; hexamethylenetetramine; glyoxal; glutardialdehyde; N-methylolchloroacetamide; 1-(hydroxymethyl)-5,5-dimethylhydantoin; imidazolidinylurea; 1-(3-chloroallyl)-3,5,7-triaza-1-azoniaadamantane chloride; 1,3-bis-($\beta$-ethylhexyl)-5-methyl-5-aminohexahydropyrimidine; 1,3,5-tris-(hydroxyethyl)-1,3,5-hexahydrotriazine; 1,2-dibromo-2,4-dicyanobutane; 5-bromo-5-nitro-1,3-dioxane; 2-bromo-2-nitropropanediol; 1,1'-hexamethylene-bis-[5-(4-chlorophenyl)-bisguanide]; 4,4-diaminodiphenoxypropane; 2-bromo-2-nitropropane-1,3-diol; sorbic acid and its salts; p-hydroxybenzoic acid and its esters and salts; zinc 2-pyridinethiol-N-oxide; 2-[(hydroxymethyl)-amino]-ethanol; dithio-2,2'-bis-(benzylamide); 5-chloro-2-(2,4-dichlorophenoxy)-phenol; thio-bis-(4-chlorophenol); o-phenylphenol; chloromethyl diiodomethyl sulfone; and p-chlorophenyl-3-iodopropargyl-formal.

19. A method for protecting a microorganism, an article, or a liquid from fungi, bacteria or algae, comprising treating said microorganism, article or liquid with a microbicidally effective amount of a 1-hydroxypyrazole derivative of the formula:

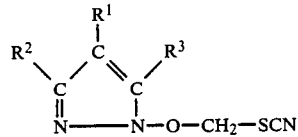

wherein $R^1$, $R^2$ and $R^3$ are each independently a hydrogen atom or a halogen atom.

20. The method of claim 19, wherein as 1-hydroxypyrazole derivative is a 4-halo-1-[(thiocyanato)-methoxy]-pyrazole.

21. The method of claim 19, wherein said 1-hydroxypyrazole derivative is 4-chloro-1-[(thiocyanato)-methoxy]-pyrazole.

* * * * *